(12) United States Patent
Havekotte et al.

(10) Patent No.: US 8,980,352 B2
(45) Date of Patent: Mar. 17, 2015

(54) CONTROL OF FLAVOR CHARACTERISTICS OF AND INDICATOR OF FRESHNESS IN FRUIT JUICE

(75) Inventors: Margaret Havekotte, Valhalia, NY (US); Thomas Hofmann, Neufahrn (DE); Anneke Glabasnia, Cormondreche (CH); Cheryl Nagle, Bradenton, FL (US); Michael J. Morello, Cary, IL (US); Todd A. Rakofsky, Crystal Lake, IL (US); Rachel L. Jordan, Palatine, IL (US)

(73) Assignee: Tropicana Products, Inc., Bradenton, FL (US)

( * ) Notice: Subject to any disclaimer, the term of this patent is extended or adjusted under 35 U.S.C. 154(b) by 956 days.

(21) Appl. No.: 12/248,621

(22) Filed: Oct. 9, 2008

(65) Prior Publication Data

US 2009/0175995 A1 Jul. 9, 2009

Related U.S. Application Data

(60) Provisional application No. 60/978,515, filed on Oct. 9, 2007.

(51) Int. Cl.
| | | |
|---|---|---|
| *C12C 3/08* | (2006.01) |
| *C12C 3/12* | (2006.01) |
| *C12C 7/00* | (2006.01) |
| *C12C 7/14* | (2006.01) |
| *C12H 1/04* | (2006.01) |
| *A23C 9/14* | (2006.01) |
| *C12H 1/14* | (2006.01) |
| *A23L 2/02* | (2006.01) |
| *A23L 2/70* | (2006.01) |
| *C07J 73/00* | (2006.01) |
| *G01N 33/14* | (2006.01) |

(52) U.S. Cl.
CPC ... *A23L 2/02* (2013.01); *A23L 2/70* (2013.01); *C07J 73/008* (2013.01); *G01N 33/14* (2013.01)
USPC .......................................... 426/422; 426/271

(58) Field of Classification Search
USPC .......................... 426/536, 492, 599, 422, 271
See application file for complete search history.

(56) References Cited

U.S. PATENT DOCUMENTS

| | | | |
|---|---|---|---|
| 2,357,895 A | * | 9/1944 | Higby ............................ 426/324 |
| 3,463,763 A | * | 8/1969 | Griffiths ......................... 528/488 |
| 3,647,476 A | | 3/1972 | Swisher |
| 3,911,103 A | | 10/1975 | Hasegawa et al. |

(Continued)

FOREIGN PATENT DOCUMENTS

| | | |
|---|---|---|
| CN | 1688212 | 10/2005 |
| EP | 0334641 A3 | 9/1989 |

(Continued)

OTHER PUBLICATIONS

Higby, "The Bitter Constituents of Navel and Valencia Oranges," Dec. 1938, Journal of American Chemical Society, vol. 60, issue 12, pp. 3013-3018.*

(Continued)

*Primary Examiner* — Humera Sheikh
*Assistant Examiner* — Tynesha McClain-Coleman
(74) *Attorney, Agent, or Firm* — Banner & Witcoff, Ltd.

(57) ABSTRACT

Control of flavor characteristics of and fresh taste in fruit juice, particularly citrus fruit juice, and especially orange juice.

3 Claims, 8 Drawing Sheets

(56) References Cited

U.S. PATENT DOCUMENTS

| | | | |
|---|---|---|---|
| 3,989,854 | A | 11/1976 | Chandler et al. |
| 4,439,458 | A | 3/1984 | Puri |
| 4,447,456 | A | 5/1984 | Hasegawa |
| 4,514,427 | A | 4/1985 | Mitchell et al. |
| 4,971,812 | A | 11/1990 | Tsen |
| 5,734,046 | A | 3/1998 | Ifuku et al. |
| 7,238,379 | B2 * | 7/2007 | Lang .............................. 426/542 |
| 2003/0064144 | A1 | 4/2003 | Chu et al. |
| 2006/0105089 | A1 * | 5/2006 | Chu et al. ....................... 426/599 |

FOREIGN PATENT DOCUMENTS

| | | |
|---|---|---|
| EP | 0 719 502 | 7/1996 |
| GB | 1134279 | 11/1968 |
| GB | 1134279 A | 11/1968 |
| IT | 1259439 B | 3/1996 |
| JP | 58-056663 A | 4/1983 |
| JP | 59-039276 A | 3/1984 |
| JP | 60-153780 A | 8/1985 |
| JP | 03-266961 A | 11/1991 |
| WO | WO2004021806 A1 | 3/2004 |
| WO | 2009049046 | 4/2009 |

OTHER PUBLICATIONS

Annex to Form PCT/ISA/206—Communication relating to the results of the Partial International Search, Jan. 23, 2009.

Database WPI Week 198319—Thompson Scientific, London—AN 1983-45680K—XP-002509236 and Japan 58 056663 A, Aichiken Seika Nogy, Apr. 4, 1983.

Database WPI Week 198415—Thompson Scientific, London—AN 1984-092069—XP-002509237 and Japan 59 039276 A, Ehimeken Seika Nogy, Mar. 3, 1984.

Database WPI Week 199639—Thompson Scientific, London—AN 1996-386968—XP-002509349 and Italy 1 259 439 B, Consiglio Naz Delle, Mar. 18, 1996.

Assar, K., "Reduced acid FCOJ," Proceedings of the 19th Annual Short Course for the Food Industry 13, U.S. Dept. of Agriculture, 1979.

Berhow, Mark A., et al., "Citrus Limonoids: Functional Chemicals in Agriculture and Food," ACS Symposium Series, 2000.

"Council Directive 2001/112/EC Relating to Fruit Juices and Certain Similar Products Intended for Human Consumption," Official Journal of the European Communities, Dec. 2001.

Dekker, Robert F. H., "De-Bittering of Citrus Fruit Juices: Specific Removal of Limonin and Other Bitter Principles," Australian Journal of Biotechnology, vol. 2, No. 1, Jun. 1988.

Guadagni, D. G., et al., "Effect of Some Citrus Juice Constituents on Taste Thresholds for Limonini and Naringin Bitterness," J. Sci Food Agric, 1973.

Guadagni, D. G., et al., "Effect of Subthreshold Concentrations of Limonin, Naringin and Sweeteners on Bitterness Perception," J. Sci Food Agric, 1974.

Johnson, Robert L., et al., Ion Exchange and Adsorbent Resins for Removal of Acids and Bitter Principles from Citrus Juices, J. Sci Food Agric, 1985.

Koch Membrane Systems, Inc., "Citrus Processing with Ultrafiltration/Adsorption Combined Technology," Citrus Seminar, Bebedouro, Brazil, Apr. 1994.

Nagy, Steven, et al., "Fruit Processing Technology," Agscience, Inc., 1993.

Rouseff, R. L., et al., "Nomilin, Taste Threshold and Relative Bitterness," J. Food Sci 1994.

Shaw, Phillip, "Citrus Juice Debittering—Current Status Worldwide," The Citrus Industry, Jun. 1990.

Ozaki, Y., et al., "Limonoid glucosides in *Tetradium rutaecarpa*," Phytochemistry, vol. 30, No. 7, 1991.

JP Office Action dated Oct. 25, 2011 in corresponding Application No. 2010-529039; English Translation.

Chinese Patent Application 200880110658.0, dated Feb. 15, 2012.

EP Application No. 12169847.6-1221—Extended European Search Report—dated Jul. 12, 2012.

Office Action received in corresponding Chinese Application No. 200880110658.0 issued on Jan. 14, 2013.

Office Action received in corresponding Korean Application No. 10-2010-7009734 issued on Dec. 20, 2012.

Office Action received in corresponding Canadian Application No. 2,700,417 issued on Dec. 31, 2012.

\* cited by examiner

CONTROL OF FLAVOR CHARACTERISTICS OF AND INDICATOR OF FRESHNESS IN FRUIT JUICE

This application claims priority to U.S. Provisional Application Ser. No. 60/978,515, filed Oct. 9, 2007, entitled Control of Flavor Characteristics of and Indicator of Freshness in Fruit Juice, and incorporated herein by reference in their entirety.

FIELD OF THE INVENTION

The invention relates to control of flavor characteristics of and fresh taste in fruit juice. In particular, the invention relates to control of flavor characteristics of and fresh taste in citrus fruit juice, and especially in orange juice.

BACKGROUND OF THE INVENTION

Citrus fruits have long been recognized as valuable sources of important nutrients. More recently, health benefits and disease-retarding or -treating benefits of citrus sources have come to be more fully recognized as advantageous and beneficial when ingested. Accordingly, there is a general belief that increasing the intake of citrus-originating foods is a beneficial and important objective in the overall scheme of human health. Citrus fruits also are enjoyed by many consumers simply because they are flavorful.

One convenient way to ingest citrus products is in the form of juice. Juice can be made easily and can be transported and consumed conveniently. Fresh, or 'not-from-concentrate' juice, is prized for its flavor and quality. Juice also can be concentrated and then reconstituted at the consumer's convenience. Concentrated juice also is distributed from the source to consumer in an efficient and cost-effective way. Also, juice may be more easily consumed than fruit by persons who have difficulty eating solid foods.

However, some consumers dislike certain characteristics of citrus juices, such as bitterness, acidity, off-flavor notes, astringency, browning, and a thick consistency. All citrus fruits, including grapefruits, oranges, tangerines, limes, and lemons, can present these concerns. Some consumers prefer juices that have a low level of sweetness, whereas others prefer a very sweet product. Further, it often is difficult to achieve consistency in the flavor characteristics, for example, from early in the season to late in the season.

Bitterness often is a primary concern for consumers. A low level of bitterness may provide a desirable contribution to the organoleptic properties and characteristics of juice for many consumers. Such consumers enjoy the piquant flavor note of a low level of bitterness. However, most consumers also agree that excessive bitterness adversely affects the organoleptic properties and characteristics of juice, making it unpleasant to consume. Consumers often also associate bitterness with lack of freshness, with concentrated juice, and/or with lower quality juice.

Bitter flavors are found in each kind of citrus fruits in varying quantities. There are differences in the concentrations of these flavors between cultivars of the same fruit and between fruits of the same cultivar from early in the season to late in the season. Therefore, the source of the fruit, the time of the season, and other variables, affect the concentrations of bitter flavors in fruit.

Astringency is a characteristic of juices, particularly citrus juices, that consumers often find objectionable. In particular, astringency in citrus juice often is characterized as a velvety, mouth-coating sensation. This mouthfeel is considered unpleasant by many consumers.

Consumers also are concerned with acidity of fruit juice. Citrus juices often are considered acidic by consumers. Consumers often associate acidity not only with an objectionably sharp taste but also with feelings of upset or discomfort in the stomach and eructation.

To date, limited efforts have been made to reduce bitterness, acidity, and other objectionable organoleptic properties and characteristics, typically by removal of selected compounds. Limonin is one such compound. Other methods exclude parts of the fruit, such as seeds and peels, from the juice source, to minimize the concentration of the bitter flavor.

Also, freshness is a characteristic desired by consumers. Often, juice from concentrate is considered to be of lower quality than fresh juice. Various methods for treating frozen juices and juice concentrates are known. However, to date, juice from concentrate suffers deleterious effects on flavor, and no completely satisfactory juice, whether fresh or frozen, has been made commercially available.

Thus, there exists a need for a juice in which bitter flavor is controlled to within limits that consumers generally find pleasing and not excessively bitter. There also exists a need for a juice that tastes fresh.

BRIEF SUMMARY OF THE INVENTION

A first embodiment of the invention relates to control of bitterness in fruit juice, especially citrus juice.

A second embodiment of the invention relates to control of bitterness and freshness in citrus juice by controlling the concentrations of key bitter flavors.

A third embodiment of the invention relates to control of astringency in fruit juice, especially orange juice.

A fourth embodiment of the invention relates to control of acidity in fruit juice, especially orange juice.

A fifth embodiment of the invention relates to control of sweetness in fruit juice, especially orange juice.

DETAILED DESCRIPTION OF THE INVENTION

The invention is directed to control of flavor characteristics of fruit juice. In particular, embodiments of the invention are directed to control of bitterness in citrus juice by controlling the concentrations of key bitter flavors, to control of astringency by controlling the cause of key astringency features, to control of acidity by controlling the concentrations and relative proportions of acids, and to control of sweetness by control of the concentrations and relative proportions of sugars.

The invention also is directed to imparting a fresh taste to juice. In particular, embodiments of the invention are directed to control of a component in fruit juice to make the juice taste fresh.

Skilled practitioners recognize that the concentration of a flavor component in a food product must exceed a threshold before a consumer will be able to sense that flavor component. The threshold for sensation of different flavor characteristics, such as astringency and bitterness, are different. Therefore, work to date on identification of compounds that contribute to flavor characteristics has been directed toward those compounds that are present at concentrations that exceed the relevant taste threshold.

The inventors have discovered that the bitter taste of citrus fruit juice, particularly of orange juice, is caused at least in part by the interplay of three bitter substance groups and is affected by the concentration of sugar in the juice. This discovery of the synergy between these three bitter substance groups and sugar forms the foundation for the ability to control bitterness in citrus juice. To date, it was not known to the skilled practitioner that three bitter substance groups and sugar controlled the sensation of bitterness in orange juice.

Limonin, a substance known to the skilled practitioner to cause bitterness in orange juice, does not by itself account for the entirety of the bitterness of orange juice. Rather, bitterness in orange juice is caused by the interplay of the following three bitter substance groups:

(1) Limonin, isolimonin, and, to a minor extent, nomilin;

(2) Polymethoxylated flavones (PMF's); and (3) Limonoid β-D-glucopyranosides.

Thus, control of the relative concentrations of these components, together with control of the sugar concentration, in juice, will control the sensation of bitterness in the juice.

The concentrations of the members of these bitter substance groups vary as a function of the cultivar, the time in the growing and harvesting season (i.e., whether early-, mid-, or late-season), and processing conditions. For example, limonin is found to develop to a greater extent in juice obtained from oranges harvested in early- and mid-season than it does when the juice is obtained from late-season harvested oranges. With an understanding of the relationship between the three bitter substance groups and sugar, the bitterness of orange juice, and of citrus juices comprising these components, can be controlled.

The taste thresholds of members of these bitter substance groups are set forth in the following table:

| Component | Bitter Taste Threshold, μmol/L |
|---|---|
| Limonin | 4 |
| Nomilin | 13 |
| PMF's | >130 |
| 5,7,8,3',4'-pentamethoxyflavone | 32.3 |
| 3,5,7,8,3',4'-hexamethoxyflavone | >250 |
| 5,6,7,3',4'-pentamethoxyflavone | 56 |
| 3,5,6,7,3',4'-hexamethoxyflavone | 19 |
| 5,7,8,4'-tetramethoxyflavone | >120 |
| 5,6,7,8,3',4'-hexamethoxyflavone | 103 |
| Limonoid β-D-glucopyranosides | >130 |
| 5,6,7,4'-tetramethoxyflavone | 44 |
| 3,5,6,7,8,3',4'-heptamethoxyflavone | 24-31 |
| 5,6,7,8,4'-pentamethoxyflavone | 93 |
| 4'-hydroxy-3',5,6,7,8-pentamethoxyflavone | 25 |
| 5,6,7,8,3',4'-Hexamethoxyflavone-3-O-β-D-glucopyranoside | 78 |
| 5,6,7,3',4'-pentamethoxy-flavone-3-O-β-D-glucopyranoside | 61 |
| 5,6,7,3',4'-pentamethoxyflavoneglucoside | 61 |
| 5,6,7,8,3',4'-hexamethoxyflavoneglucoside | 78 |
| 5,7,8,3',4'-pentamethoxyflavone | 32 |
| 5,6,7,3',4'-pentamethoxyflavone | 56 |
| 3,5,6,7,3',4'-hexamethoxyflavone | 19 |
| 5,6,7,8,3',4'-hexamethoxyflavone | 103 |
| 5,6,7,4'-tetramethoxyflavone | 150 |
| 7,3',4'-trimethoxyflavone | >400 |
| 7,8,3',4'-tetramethoxyflavone | >400 |
| Limonin-17-β-D-glucopyranoside | 106 |
| Deacetylnomilinic acid-17-β-D-glucopyranoside | 68 |
| Epiisoobacunoic acid 17-β-D-glucopyranoside | 42 |
| Nomilin acid β-glpc | >800 |
| Nomilin β-glpc | >700 |
| Obacunon β-glpc | 49 |
| Deacetylnomilin | >106 |

As can be seen in the structural formulas of these compounds, the members of these bitter substance groups have common structural features.

The inventors have discovered that subthreshold concentrations of PMF's and, to a minor extent, nomilin, enhance the limonin-induced bitterness in orange products such as juice. This effect is surprising, because the skilled practitioner would not expect that a compound that is present below the taste threshold would contribute to bitterness.

Nomilin is near threshold concentration in Hamlin orange juice, and may reach threshold early in the season. Limonoid β-D-glucopyranosides are above threshold in both Hamlin and Valencia orange juice.

These members of these bitter substance groups are very bitter. In particular, they are significantly more bitter than compounds typically found in carbonated soft drinks and tea. For example, limonin is nearly 200 times more bitter than caffeine and 150 times more bitter than catechin. Nomilin is nearly 150 times more bitter than caffeine and 45 times more bitter than catechin.

Whereas each member of a bitter substance groups has a taste threshold, bitterness is not linearly related to concentration. For example, doubling the concentration of the component does not double the bitterness. Further, the inventors have discovered that the concentration of a compound need not reach the taste threshold for that compound to make a contribution to bitterness. Rather, the components act synergistically to yield a bitter taste greater than the sum of the individual parts would predict.

Sugar is measured in degrees Brix. The inventors have discovered that perceived bitterness goes down as Brix is increased, and in particular as the Brix/acid ratio is increased.

Thus, with the guidance provided herein, the skilled practitioner can control the bitterness of citrus juice by controlling the Brix, and in particular, the Brix/acid ratio, and the concentrations of these members of these bitter substance groups in a juice product. For example, the concentration of these compounds can be reduced with appropriate processing, such as ion exchange, distillation, or reverse osmosis. Similarly, different juices having various concentrations of each compound can be blended to yield a juice that has concentrations of these compounds lower than the concentrations that result in a bitter taste.

The inventors have discovered that limonin is formed by various pathways. Limonin typically is not found in whole fruit at a concentration above the taste threshold. However, limonin is formed by lactonization accelerated by enzymes.

Figure 1:
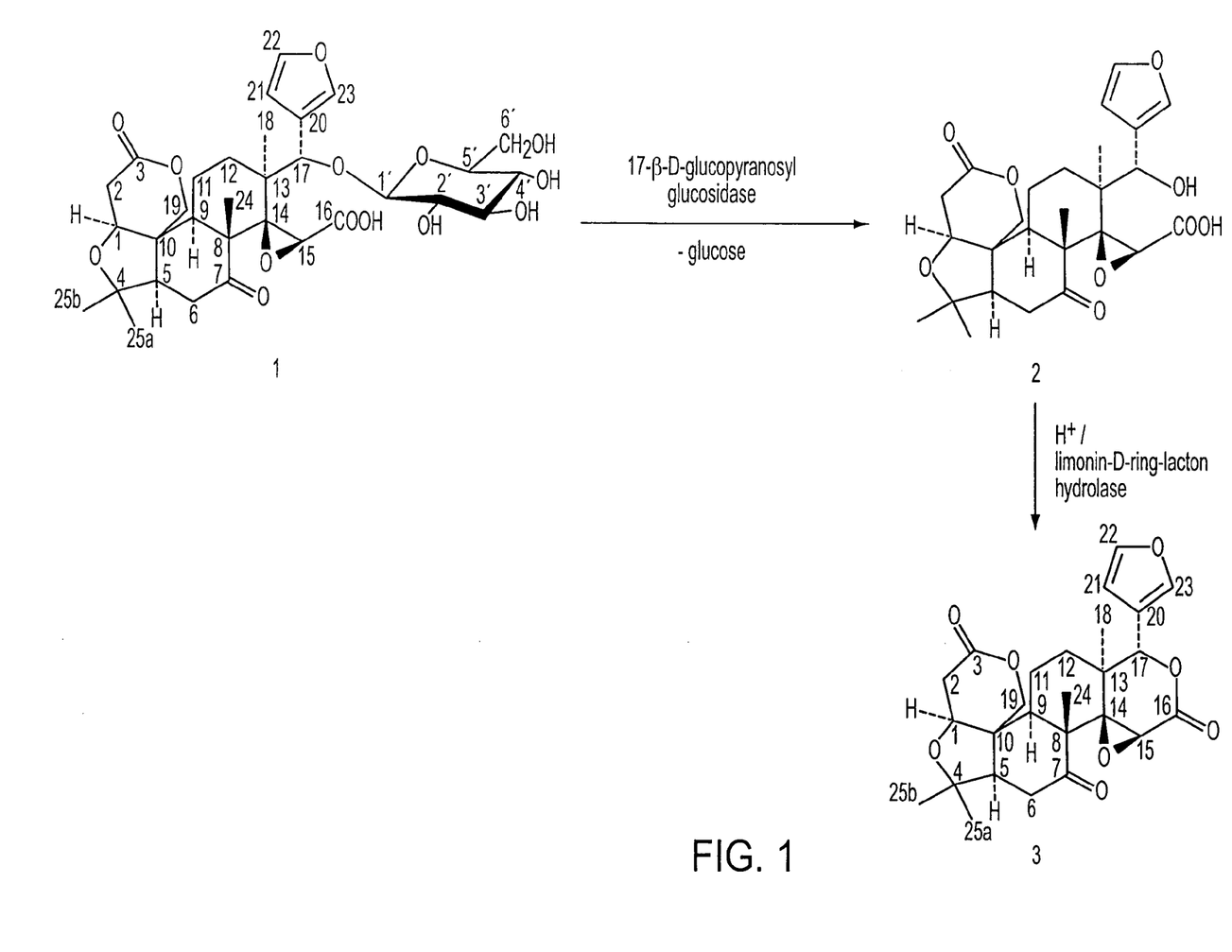
FIG. 1 depicts a reaction scheme showing the enzymatic degradation of limonin-17-β-D-glucopyranoside (1) via the limonoate A-ring lactone (2) to give the bitter tasting limonin (3).

FIG. 1 illustrates this pathway. Limonin-17-β-D glucopyranoside 1 is converted by the action of 17-β-D-glucopyranosyl glucosidase to form a limonate A-ring lactose 2. This lactone is reduced in the presence of limonin-D-ring lactone hydrolase under acid conditions (pH<6.5) to form limonin 3. Because the A-ring lactone is converted to limonin-17-β-D-glucopyranocide as the fruit ripens, the concentration of glucoside builds to about 200 wppm.

It also is believed that limonin may be generated in juice through acid hydrolysis. This acid hydrolysis is accelerated by decreased pH and increased temperature and time. Thus, other methods for controlling limonin in juice are to avoid heating, to store juice for limited time at low temperature, and/or to increase the pH of the juice.

The concentration of each member of the bitter substance groups can be determined by high pressure liquid chromatography (HPLC). However, liquid chromatography/mass spec (LCMS) analysis or LCMS/MS analysis would provide more definitive measurement. The skilled practitioner understands these and other methods of measuring the concentrations of the members of the bitter substance groups.

The inventors have discovered that, as with bitterness, a plurality of compounds present in orange juice below the astringency threshold contributes to the astringent mouth feel of the juice. The taste thresholds for these astringent compounds individually are set forth in the following table:

| Component | Astringency Taste Threshold, μmol/L |
|---|---|
| 5,7,8,3',4'-pentamethoxyflavone | 13.3 |
| 3,5,7,8,3',4'-hexamethoxyflavone | 125 |
| 5,6,7,3',4'-pentamethoxyflavone | 24 |
| 3,5,6,7,3',4'-hexamethoxyflavone | 9 |
| 5,7,8,4'-tetramethoxyflavone | 44 |
| 5,6,7,8,3',4'-hexamethoxyflavone | 51 |
| 5,6,7,4'-tetramethoxyflavone | 21 |
| 3,5,6,7,8,3',4'-heptamethoxyflavone | 4-5 |
| 5,6,7,8,4'-pentamethoxyflavone | 19 |
| 4'-hydroxy-3',5,6,7,8-pentamethoxyflavone | 6 |
| 5,6,7,8,3',4'-Hexamethoxyflavone-3-O-β-D-glucopyranoside | 20 |
| 5,6,7,3',4'-pentamethoxyflavone-3-O-β-D-glucopyranoside | 21 |
| 5,6,7,3',4'-pentamethoxyflavoneglucoside | 21 |
| 5,6,7,8,3',4'-hexamethoxyflavoneglucoside | 20 |
| 5,7,8,3',4'-pentamethoxyflavone | 13 |
| 5,6,7,3',4'-pentamethoxyflavone | 24 |
| 3,5,6,7,3',4'-hexamethoxyflavone | 9 |
| 5,6,7,8,3',4'-hexamethoxyflavone | 51 |
| 5,6,7,4'-tetramethoxyflavone | 31 |
| 7,3'-trimethoxyflavone | 15 |
| 7,8,3',4'-tetramethoxyflavone | 44 |
| Limonin-17-β-D-glucopyranoside | 17 |
| Deacetylnomilinic acid-17-β-D-glucopyranoside | 27 |
| Epiisoobacunoic acid 17-β-D-glucopyranoside | 16 |
| Deacetylnomilin | 13.2 |
| Limonin | 4 |
| Isolimonin | 10 mg/L |

Thus, with the guidance provided herein, the skilled practitioner can control the astringency of citrus juice by controlling the concentrations of these astringent compounds in a juice product. For example, the concentration of these compounds can be reduced with appropriate processing, such as ion exchange, distillation, or reverse osmosis. Similarly, different juices having various concentrations of each compound can be blended to yield a juice that has concentrations of these compounds lower than the concentrations that result in an astringent taste.

Acidity also is of concern to consumers. An acid-tasting product is unpleasant and has a sharp taste. Further, acidity often causes stomach upset and damage to the stomach and esophagus and eructation.

The inventors have discovered that perceived acidity is related to the relative concentrations of at least malic acid and citric acid. The concentrations and relative proportions of these compounds affect the perceptions of acidity.

The acid taste thresholds for malic acid and for citric acid are known in the art. Although the relative proportions of these acids vary between juices of different cultivars and with time in season, the acids typically are above acid taste threshold and so contribute to acid taste sensation.

Thus, with the guidance provided herein, the skilled practitioner can control the acidity of citrus juice by controlling the concentrations of these acids in a juice product. For example, the concentration of these acids can be reduced with appropriate processing, such as ion exchange, distillation, or reverse osmosis. Similarly, different juices having various concentrations of each acid can be blended to yield a juice that has concentrations of these acids lower than the concentrations that result in an acidic taste.

Sweetness also is of concern to consumers. Whereas some consumers prefer a sweet taste, others do not. Therefore, the ability to control sweetness presents the opportunity to increase consumer satisfaction.

The inventors have discovered that perceived sweetness is related to the relative concentrations of at least the sugars glucose, fructose, and sucrose. The concentrations and relative proportions of these sugars affect the perception of sweetness.

The sweet taste threshold for the glucose, fructose, and sucrose are known in the art. The relative proportions of these sugars vary between juices of different cultivars and with time in season. However, with the guidance provided herein, the skilled practitioner can control the sweetness of citrus juice by controlling the concentrations of these sugars in a juice product. For example, the concentration of these sugars can be reduced with appropriate processing, such as ion exchange, distillation, or reverse osmosis. Similarly, different juices having various concentrations of each compound can be blended to yield a juice that has concentrations of these compounds lower than the concentrations that result in an acidic taste.

The inventors also have discovered that the presence of isolimonin, a compound formed from one of these limonoid β-D-glucopyranosides, is an indicator of freshness. Isolimonin also is known as $C_{17}$-epilimonin. Isolimonin is formed by acid hydrolysis of limonin after pasteurization. Isolimonin also is formed non-enzymatically from limonin 17-β-D-glucopyranoside. The concentration of isolimonin in frozen orange juice concentrate is about twice that of fresh orange juice, indicating that 'stressing' the juice also contributes to isolimonin formation. Thus, the presence of isolimonin at a concentration higher than that of fresh product indicates that the product may not be fresh (because isolimonin forms over time) or has been frozen.

EXAMPLES

The following examples illustrate various aspects related to the invention. Example 1 is directed to isolation of limonin-17-β-D-glucopyranoside from orange seeds. Example 2 summarizes studies at various temperatures and pH values to determine the rate at which limonin was developed in solutions. Identification of limonin and isolimonin by HPLC and LC-MS and NMR is set forth in Example 3.

Example 4 is directed to quantification of limonin and isolimonin in orange juice. Example 5 is directed to sensory analysis.

For these examples, the following compounds were obtained commercially: limonin (Sigma, Steinheim, Germany); formic acid, methanol, and acetonitrile (Merck, Darmstadt, Germany); deuterated solvents (Aldrich, Taufkirchen, Germany); deionized water used for chromatography was purified by means of a Milli-Q Gradient A10 system (Millipore, Billerica, USA). Orange seeds and orange juice prepared from oranges (Valencia late) harvested in Florida (USA) in March 2006 as well as frozen concentrated orange juice prepared from the same batch of fruits were obtained from the orange juice industry (USA). Fresh orange fruits (Valencia late) were purchased from a local vendor.

High Performance Liquid Chromatography (HPLC)

The HPLC apparatus consisted of two pumps (Sykam, S 1122), a gradient mixer (Sunchrom, dynamic/statistic gradient mixer), a Rheodyne injector (250 µL loop), an autosampler (Spark, Midas 380), a diode array detector (Sunchrom, SpectraFlow 600 DAD), monitoring the effluent in a wavelength range between 200 and 600 nm, a splitting module (Upchurch, P-470 graduated microsplitter), and an evaporative light scattering detector (ELSD) (S.E.D.E.R.E., Sedex 85 LT-ELSD, p=2.6 bar, T=40° C.) equipped with a nebulizer (S.E.D.E.R.E., HPLC nebulizer 200 µL/min-2.5 mL/min).

Liquid Chromatography/Mass Spectrometry (LC/MS)

LC-MS/MS analysis was performed using an Agilent 1100 HPLC-system connected to the API 4000 LC-MS/MS (Applied Biosystems, Darmstadt, Germany) running either in the negative (ESI$^-$) or positive electrospray ionization (ESI$^+$) mode. The spray voltage was set at −4500 V, nitrogen served as curtain gas (20 psi) and declustering potential was set at −65 V. By means of the multiple reaction monitoring (MRM) mode, compounds 2 and 3 were analyzed using the mass transitions described above.

Nuclear Magnetic Resonance Spectroscopy (NMR)

The $^1$H, COSY, HMQC, and HMBC spectroscopic experiments were performed on DPX 400 MHz NMR from Bruker (Rheinstetten, Germany). Samples were dissolved in DMSO-d$_6$ or MeOD-d$_4$ with tetramethylsilane as internal standard and placed into NMR tubes (Schott Professional 178×5 mm) prior to measurement. Data processing was performed by using the NMR Software Mestre-C.

Example 1

Isolation of Limonin-17-β-D-glucopyranoside from Orange Seeds

Orange seeds (100 g) were washed thoroughly with water, followed by acetone, and were frozen in liquid nitrogen, crushed in a grinding mill, and then extracted twice with methanol (300 mL) for 4 h at 60° C. After filtration, the extract was freed from solvent in vacuum yielding the methanol extractables as an amorphous powder (28 g).

An aliquot (2 g) of that crude isolate was taken up in water (10 mL) applied onto the top of a water-cooled glass column (300 mm×35 mm) filled with a slurry of Amberlite XAD-2 material (BDH Chemicals Ltd, Poole, England) conditioned with water. Operating at a flow rate of 5 mL/min, chromatography was performed starting with water (200 mL; fraction I), followed by methanol/water mixtures containing 20% (200 mL; fraction II), 40% (200 mL; fraction III), 60% (200 mL; fraction IV), 80% (200 mL, fraction V), and methanol (200 mL; fraction VI). The individual fractions were collected separately, freed from solvent in vacuum at 30° C., and were then freeze-dried to afford fractions I-VI as amorphous powders.

Fractions II-IV were combined, dissolved in mixture (20/80, v/v) of methanol and 0.1% aqueous formic acid, and, after membrane filtration, aliquots (250 µL) were fractionated by semi-preparative HPLC on a Microsorb-MV, RP-18, 250×10 mm i.d., 5 µm column (Varian, Germany). Monitoring the effluent by means of an UV detector at 220 nm as well as by an evaporative light scattering detector (ELSD), chromatography was performed at a flow rate of 3.5 mL/min starting with mixture (10/90, v/v) of acetonitrile and 0.1% aqueous formic acid, increasing the acetonitrile content to 20% within 15 min, holding for 5 min, and, finally, raising the acetonitrile content to 100% within 5 min. The effluent of the peak detected at 17 min was collected in an ice-cooled flask, the organic solvent was removed in vacuum, and the aqueous layer was applied onto the top of Strata C 18-E SPE cartridge (10 g, 55 µm; Giga Tubes, Phenomenex) conditioned with water. The cartridge was flushed with water (150 mL), then dried by sucking a stream of nitrogen through it, and, finally, eluted with methanol (100 mL). The SPE cartridge removes formic acid traces to prevent proton-catalyzed liberation of the aglycon. The organic effluent was freed from solvent in vacuum, the residue was suspended in water (5 mL) and freeze-dried to afford limonin-17-β-D-glucopyranoside as a white amorphous powder with a purity of more than 99%.

Limonin-17-β-D-glucopyranoside, 1 in FIG. 1: UV/VIS (acetonitrile/water; pH 2.5): $\lambda_{max}$=220 nm; LC/MS (ESI$^+$): m/z 649 ([M-H]$^-$); LC/MS (ESI$^-$): m/z 668 ([M+NH$_4$]$^+$), 673 ([M+Na]$^+$), 689 ([M+K]$^+$); $^1$H NMR (400 MHz, MeOD-d$_4$, COSY): δ 0.66 [s, 3H, H—C(24)], 0.98 [s, 3H, H—C(25b)], 1.21 [s, 3H, H—C(25a)], 1.40 [s, 3H, H—C(18)], 1.66 [m, 1H, H—C(12)], 1.78 [m, 2H, H—C(11)], 1.99 [m, 1H, H—C(12)], 2.43 [dd, 1H, J=7.4, 22.1 Hz, H—C(6)], 2.55 [dd, 1H, J=5.6, 19.0 Hz, H—C(6)], 2.68 [d, 1H, J=4.3 Hz, H—C(9)], 2.71 [d, 2H, J=4.1 Hz, H—C(2)], 2.79 [dd, 1H, J=5.6, 14.7 Hz, H—C(5)], 2.94 [s, 1H, H—C(15)], 3.11 [m, 2H, H—C(2'), H—C(5')], 3.20 [m, 1H, H—C(4')], 3.27 [m, 1H, H—C(3')], 3.48 [m, 1H, H—C(6')], 4.20 [s, 1H, H—C(1)], 4.29 [d, 1H, J=7.6 Hz, H—C(1')], 4.40 [d, 2H, J=8.1 Hz, H—C(19)], 5.42 [s, 1H, H—C(17)], 6.53 [d, 1H, J=1.3 Hz, H—C(21)], 7.24 [s, 1H, H—C(23)], 7.63 [s, 1H, H—C(22)]; $^{13}$C NMR (100 MHz, MeOD-d$_4$, HMQC, HMBC): δ 17.1 [C, C(11)], 18.4 [C, C(24)], 20.8 [C, C(25b)], 24.7 [C, C(18)], 26.8 [C, C(12)], 29.2 [C, C(25a)], 35.2 [C, C(2)], 36.4 [C, C(6)], 44.8 [C, C(13)], 45.1 [C, C(9)], 45.2 [C, C(10)], 50.7 [C, C(8)], 54.8 [C, C(5)], 59.8 [C, C(15)], 61.7 [C, C(6')], 63.8 [C, C(19)], 69.1 [C, C(14)], 70.4 [C, C(4')], 75.4 [C, C(2')], 76.0 [C, C(5')], 76.9 [C, C(3')], 78.1 [C, C(17)], 78.4 [C, C(1)], 80.8 [C, C(4)], 104.3 [C, C(1')], 112.3 [C, C(21)], 125.4 [C, C(20)], 140.3 [C, C(22)], 142.3 [C, C(23)], 173.0 [C, C(3), C(16)], 209.6 [C, C(7)].

Example 2

Development of Limonin from Limonin-17-β-D-glucopyranoside

Figure 2:
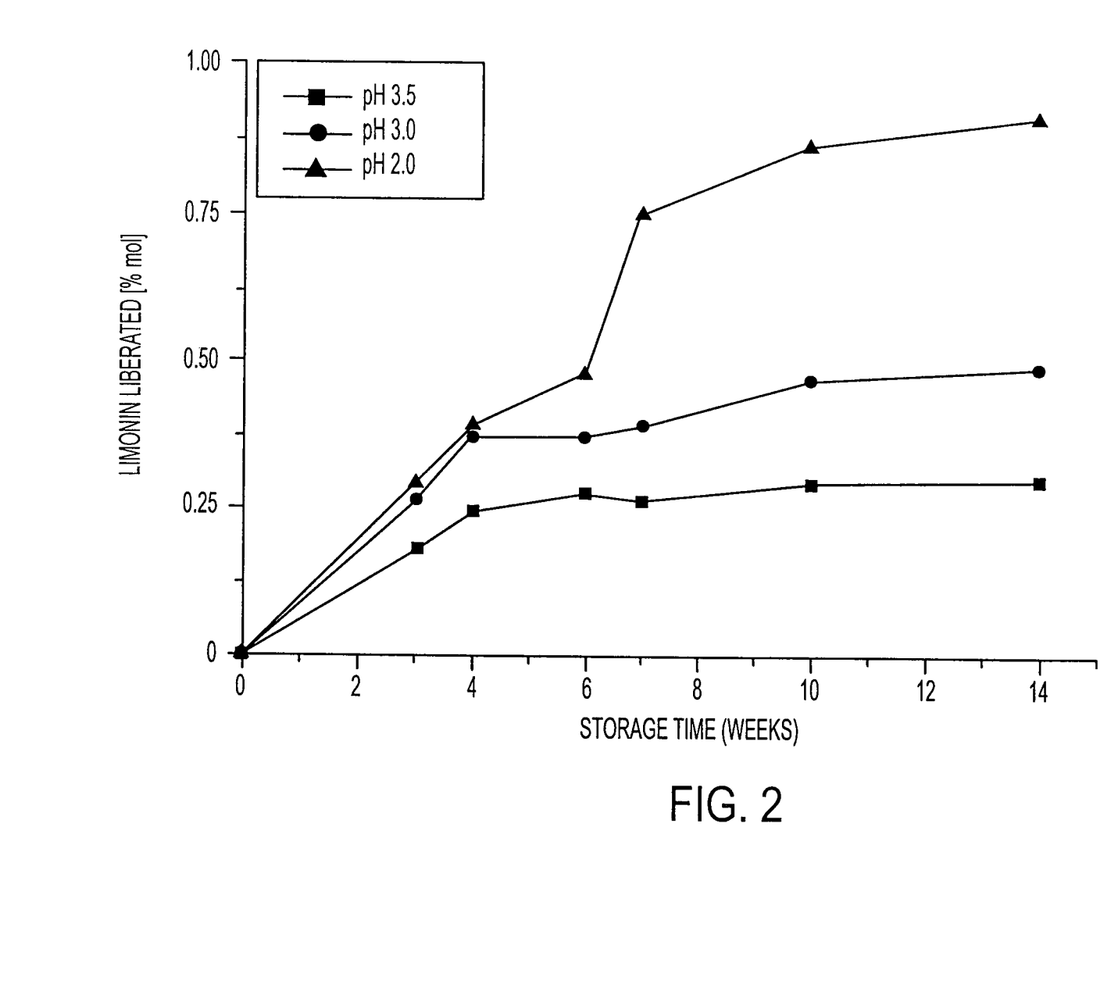
FIG. 2 illustrates the influence of the pH value on the time-dependent formation of limonin (3) in an aqueous solution of limonin-17-β-D-glucopyranoside (1) stored at 20° C.

To investigate the putative non-enzymatic release of limonin from limonin-17-β-D-glucopyranoside during storage of orange juice, aqueous solutions of the glucopyranoside adjusted to the pH value of a freshly squeezed orange juice (pH 3.5) or to the range of pH values found for orange juice concentrates (pH 2.0 and 3.0) were held at 20° C. for up to 14 weeks in the dark. At regular time intervals, aliquots were withdrawn from the model solutions and analyzed for the amount of limonin liberated from the glucopyranoside by means of HPLC-MS/MS operating in the MRM mode. Independent from the pH value of the model solution, the limonin was generated with increasing storage time, as shown in FIG. 2, but decreasing pH values favored the production of the bitter compound. For example, 0.85% mol of limonin was released from the glucopyranoside when maintained at pH 2.0, whereas at pH 3.5 only 0.25% of the bitter compound was generated.

Figure 3:
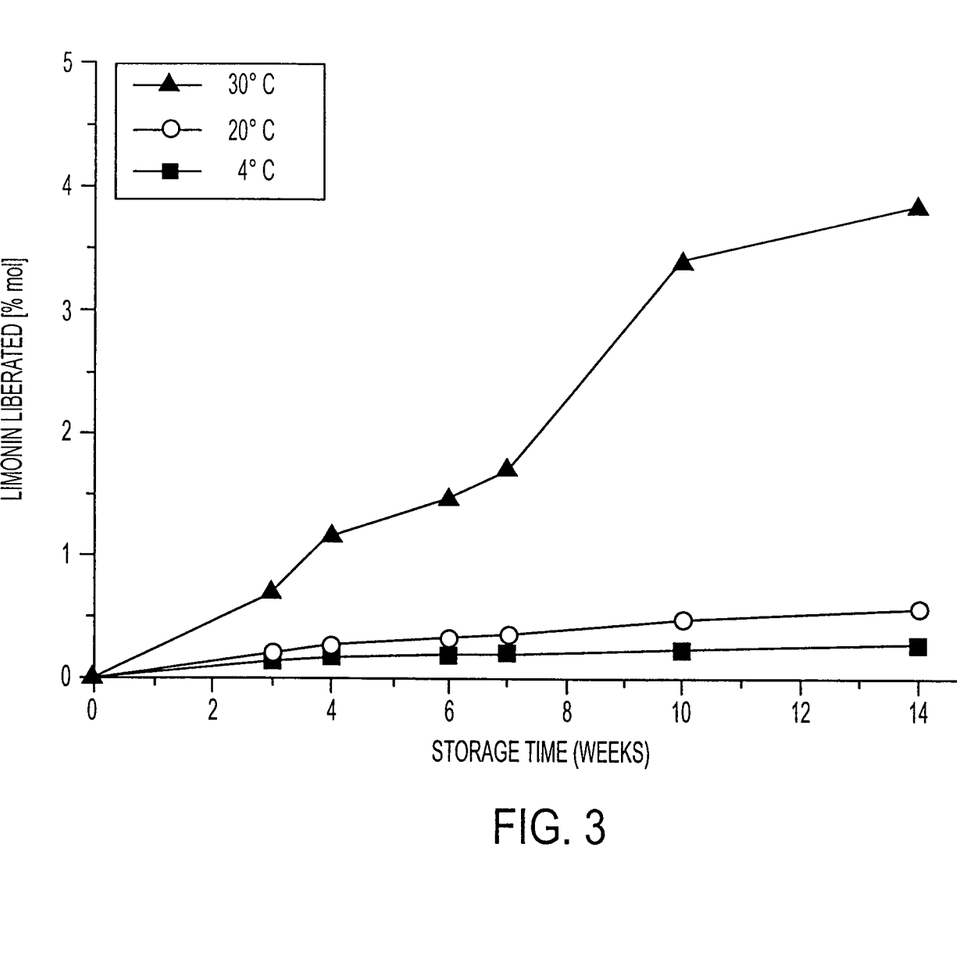
FIG. 3 illustrates the influence of the temperature on the time-dependent formation of limonin (3) in an aqueous solution of limonin-17-β-D-glucopyranoside (1) at pH 3.0.

In order to investigate the influence of the temperature on limonin generation, aqueous solutions of the glucopyranoside adjusted to pH 3.0 were maintained at 4, 20, and 30° C. for up to 14 weeks in the dark. At regular time intervals, the amounts of limonin were determined by means of HPLC-MS/MS operating in the MRM mode. The results set forth in FIG. 3 clearly demonstrated that the liberation of limonin from limonin-17-β-D-glucopyranoside was accelerated at 30° C. when compared to the model solutions kept at 4 and 20° C., respectively. For example, limonin was released from its precursor in a yield of nearly 4.0% when incubated at 30° C., whereas only 0.2% of the bitter compound was detectable after storing the precursor solution at 4° C. for 14 weeks.

In particular, aqueous solutions of limonin-17-β-D-glucopyranoside (0.35 mg/L) adjusted to pH value of 2.0, 3.0, and 3.5, respectively, by adding trace amounts of hydrochloric acid (1 mol/L) were maintained at different temperatures (4, 20, 30° C.) for up to 14 weeks in closed vials in the dark. At regular time intervals, samples (5 µL) were withdrawn with a syringe and were analyzed for the generation of limonin by means of LC-MS/MS on a Synergi Fusion, 150×2 mm i.d., 4 µm column (Phenomenex). To achieve this, chromatography was performed with a flow rate of 250 µL/min starting with a mixture (80/20, v/v) of 0.1% aqueous formic acid and acetonitrile, increasing the acetonitrile content to 40% within 10 min, then to 80% within 5 min, held for 5 min, and, finally, to 100% within 5 min. Using negative electrospray ionization, limonin was analyzed in the multiple reaction monitoring (MRM) mode using the mass transition m/z 469→229. Quantitative analysis was performed by comparing the peak areas obtained for the mass trace with those of defined standard solutions of limonin in methanol.

Figure 4:
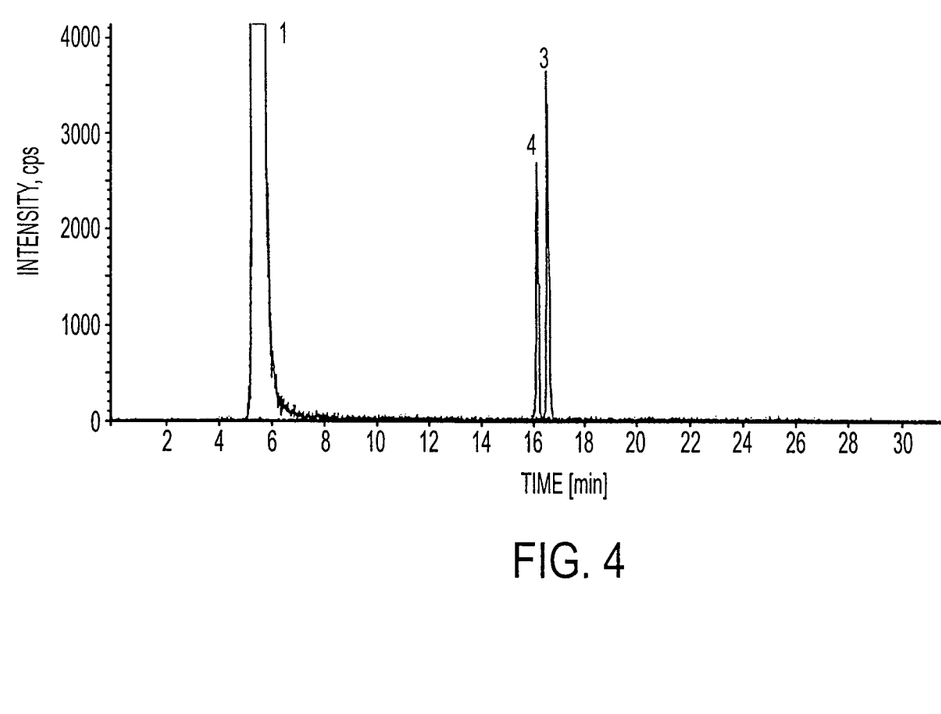
FIG. 4 is an RP-HPLC-MS/MS chromatogram obtained from an aqueous solution (pH 3.0) of limonin-17-β-D-glucopyranoside (1) incubated for ten weeks at 30° C. and showing the peaks of limonin (3) and an unknown hydrolysis product (4).

FIG. 4 illustrates that the LC-MS/MS chromatogram did not show just the limonin-17-β-D-glucopyranoside (1) and the limonin (3), but surprisingly a third peak (4) eluting at 16.59 min and showing the same mass transition m/z 469→229 as found for limonin, thus implying the existence of a limonin stereoisomer. As the chemical structure of that compound was as yet not unequivocally confirmed by NMR spectroscopic experiments, additional experiments were aimed at producing compound 4 in suitable amounts in order to perform spectroscopic experiments.

Example 3

Identification of Limonin and Isolimonin (Compound 4)

Released from Limonin-17-β-D-Glucopyranoside

Figure 5:
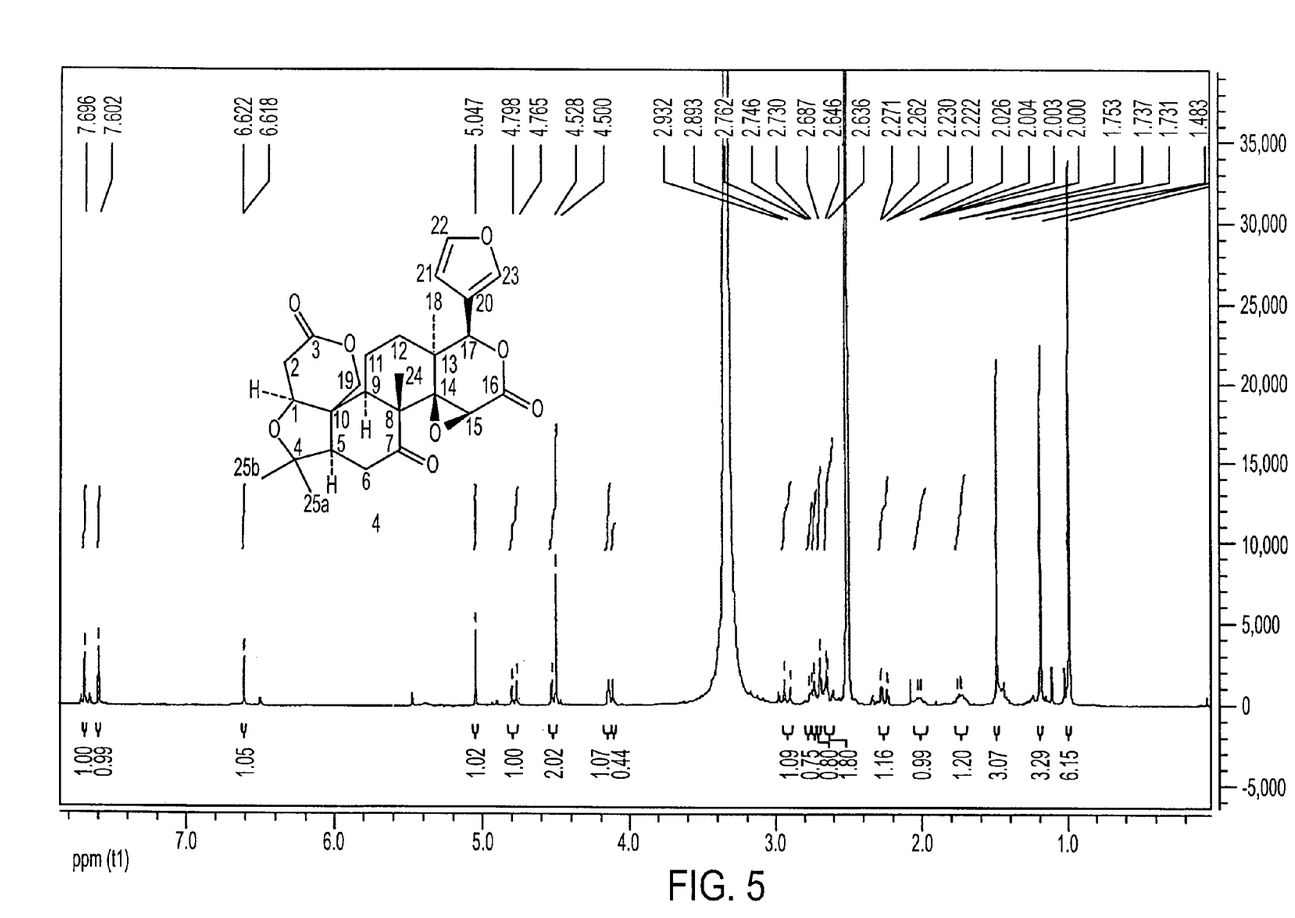
FIG. 5 is an $^1$H NMR spectrum (400 MHz) of purified $C_{17}$-epilimonin (4).

To determine the chemical structure of compound 4 identified in Example 2 and illustrated in FIG. 4, an aqueous solution of limonin-17-β-D-glucopyranoside, adjusted to pH 1.5, was incubated for 4 h at 60° C., compound 4 was isolated and purified by means of semi-preparative HPLC, and its chemical structure was determined by means of LC-MS/MS and 1D/2D-NMR experiments. In the $^1$H NMR spectrum, shown in FIG. 5, 21 signals were observed, amongst which ten signals showing chemical shifts of δ 1.44, 1.72, 2.00, 2.25, 2.66, 2.66, 2.73, 2.75, 2.91, and 4.14 ppm were rather well in line with the resonances of the alkyl protons H—C(12a), H—C(11), H—C(12b), H—C(6a), H—C(2a), H—C(5), H—C(2b), H—C(9), H—C(6b), and H—C(1) of limonin. The assignments of these signals were unequivocally confirmed by means of homo-(COSY) and hetereonuclear correlation experiments (HMQC, HMBC). The diastereotropic protons resonating at 4.51 and 4.78 ppm were well in line with the methylene protons H—C(19), thus indicating an intact A-ring as present in limonin. Also the resonance signals observed at 6.62, 7.60, and 7.70 ppm for the furan protons H—C(21), H—C(22), and H—C(23) demonstrated the structural similarity to limonin. However, compound 4 showed eye-catching differences to limonin in the chemical shifts of the protons H—C(15), H—C(17), and H—C(18). Proton H—C(17) showed a high-field shift from 5.48 ppm (3) to 5.05 ppm (4), whereas the protons H—C(15) and H—C(18) showed a low-field shift from 4.21 and 1.11 ppm (3) to 4.50 and 1.48 ppm (4), respectively. In addition, 2D-NMR experiments identified differences in the chemical shifts of C(17)/C(18) resonating at 77.9/20.0 ppm for limonin (3) and 85.1/27.1 ppm for compound 4, thus indicating an epimerization of limonin at position C(17) in the structure of compound 4. Taking all the spectroscopic data into consideration, compound 4 was unequivocally identified for the first time as the $C_{17}$-epimer of limonin displaying the furan ring at C(17) in a β-orientation rather than the α-orientation of limonin. Although compound 4, named $C_{17}$-epilimonin or isolimonin, has been speculated already as a human plasma metabolite of limonin-17-β-D-glucopyranoside, this is the first confirmation of the structure of that limonin epimer based on spectroscopic data and demonstrating its hydrolytic liberation from the glucopyranoside.

In particular, a solution of limonin-17-β-D-glucopyranoside (35 mg) in water (20 mL) was adjusted to pH 1.5 with trace amounts of hydrochloric acid (1 mol/L) and incubated for 4 h at 60° C. After cooling, the solution was applied on top of a water-conditioned Strata C 18-E SPE cartridge (10 g, 55 µm, Giga Tubes, Phenomenex), then flushed with water (150 mL), followed by a water/methanol mixture (50/50, v/v; 100 mL), and methanol (150 mL). The methanol fraction was freed of solvent in vacuum, dissolved in a mixture of methanol and 1% aqueous formic acid, and aliquots (100 µL) were separated by means of a semi-preparative HPLC on Microsorb-MV, RP-18, 250×10 mm i.d., 5 µm column (Varian, Germany). Monitoring the effluent by means of a UV-detector at 220 nm as well as an ELSD, chromatography was performed by a solvent gradient operated at a flow rate of 3.5 mL/min and starting with mixture (30/70, v/v) of acetonitrile and 0.1% aqueous formic acid, increasing the acetonitrile content to 40% within 15 min, then to 80% within 10 min, and, finally, to 100% within 10 min. Two peaks were detectable; the effluent of each peak was separately collected in ice-cooled flasks, freed from solvent in vacuum, and then freeze-dried. The isolated compounds were identified by means of LC-MS and NMR experiments as limonin and its previously not reported stereoisomer $C_{17}$-epilimonin, also known as isolimonin.

Limonin, 3: UV/VIS (acetonitrile/water; pH 2.5) $\lambda_{max}$=220 nm; LC/MS (ESI$^+$) m/z 509 ([M+K]$^+$), 493 ([M+Na]$^+$), 488 ([M+NH$_4$]$^+$); LC/MS (ESI$^-$): m/z 469 ([M-H]$^-$); $^1$H NMR (400 MHz, DMSO-d$_6$, COSY): δ 1.00 [s, 3H, H—C(24)], 1.02 [s, 3H, H—C(25b)], 1.11 [s, 3H, H—C(18)], 1.19 [s, 3H, H—C(25a)], 1.23 [m, 1H, H—C(12)], 1.73 [m, 2H, H—C(11)], 1.83 [m, 1H, H—C(12)], 2.27 [dd, 1H, J=3.0, 14.7 Hz, H—C(6)], 2.46 [dd, 1H, J=3.0, 15.7 Hz, H—C(5)], 2.55 [m, 1H, H—C(9)], 2.62 [m, 1H, H—C(2)], 2.77 [d, 1H, J=16.4 Hz, H—C(2)], 3.10 [t, 1H, J=15.5 Hz, H—C(6)], 4.11 [m, 1H, H—C(1)], 4.12 [s, 1H, H—C(15)], 4.48 [d, 1H, J=12.9 Hz, H—C(19)], 4.92 [d, 1H, J=12.9 Hz, H—C(19)], 5.48 [s, 1H, H—C(17)], 6.51 [s, 1H, H—C(22)], 7.66 [s, 1H, H—C(21)], 7.72 [s, 1H, H—C(23)]; $^{13}$C NMR (100 MHz, MeOD-d$_4$, HMQC, HMBC): δ 17.4 [C, C(24)], 18.1 [C, C(11)], 20.0 [C, C(18)], 20.4 [C, C(12)], 22.3 [C, C(25b)], 30.1 [C, C(25a)], 35.9 [C, C(2)], 36.5 [C, C(6)], 37.5 [C, C(13)], 45.7 [C, C(10)], 46.9 [C, C(9)], 50.5 [C, C(8)], 54.3 [C, C(15)], 58.2 [C, C(5)], 65.3 [C, C(19)], 67.4 [C, C(14)], 77.9 [C, C(17)], 78.9 [C, C(1)], 80.4 [C, C(4)], 110.9 [C, C(22)], 120.6 [C, C(20)], 141.9 [C, C(23)], 143.9 [C, C(21)], 168.7 [C, C(16)], 170.9 [C, C(3)], 208.5 [C, C(7)].

$C_{17}$-Epilimonin, or isolimonin 4: UV/VIS (acetonitrile/water; pH 2.5) $\lambda_{max}$=220 nm; LC/MS (ESI$^+$) m/z 509 ([M+K]$^+$), 493 ([M+Na]$^+$), 488 ([M+NH$_4$]$^+$); LC/MS (ESI$^-$): m/z 469 ([M-H]$^-$); $^1$H NMR (400 MHz, DMSO-d$_6$, COSY): δ 0.99 [s, 3H, H—C(24)], 0.99 [s, 3H, H—C(25b)], 1.19 [s, 3H, H—C(25a)], 1.44 [m, 1H, H—C(12)], 1.72 [m, 2H, H—C(11)], 2.00 [m, 1H, H—C(12)], 2.25 [dd, 1H, J=3.7, 16.2 Hz, H—C(6)], 2.66 [m, 1H, H—C(2)], 2.66 [m, 1H, H—C(5)], 2.73 [m, 1H, H—C(2)], 2.75 [m, 1H, H—C(9)], 2.91 [t, 1H, J=15.8 Hz, H—C(6)], 4.14 [d, 1H, J=3.68 Hz, H—C(1)], 4.50 [s, 1H, H—C(15)], 4.51 [d, 1H, J=13.2 Hz, H—C(19)], 4.78 [d, 1H, J=13.2 Hz, H—C(19)], 5.05 [s, 1H, H—C(17)], 6.62 [s, 1H, H—C(22)], 7.60 [s, 1H, H—C(21)], 7.70 [s, 1H, H—C(23)]; $^{13}$C NMR (100 MHz, MeOD-d$_4$, HMQC, HMBC): δ 18.3 [C, C(11)], 19.3 [C, C(24)], 22.1 [C, C(12)], 22.1 [C, C(25b)], 27.1 [C, C(18)], 30.6 [C, C(25a)], 36.6 [C, C(2)], 36.9 [C, C(6)], 40.3 [C, C(13)], 45.0 [C, C(9)], 45.1 [C, C(10)], 47.6 [C, C(8)], 56.3 [C, C(5)], 56.6 [C, C(15)], 65.4 [C, C(19)], 70.4 [C, C(14)], 79.1 [C, C(1)], 79.9 [C, C(4)], 85.1 [C, C(17)], 112.9 [C, C(22)], 122.4 [C, C(20)], 143.8 [C, C(21)], 144.2 [C, C(23)], 168.8 [C, C(16)], 170.5 [C, C(3)], 208.3 [C, C(7)].

Figure 6:
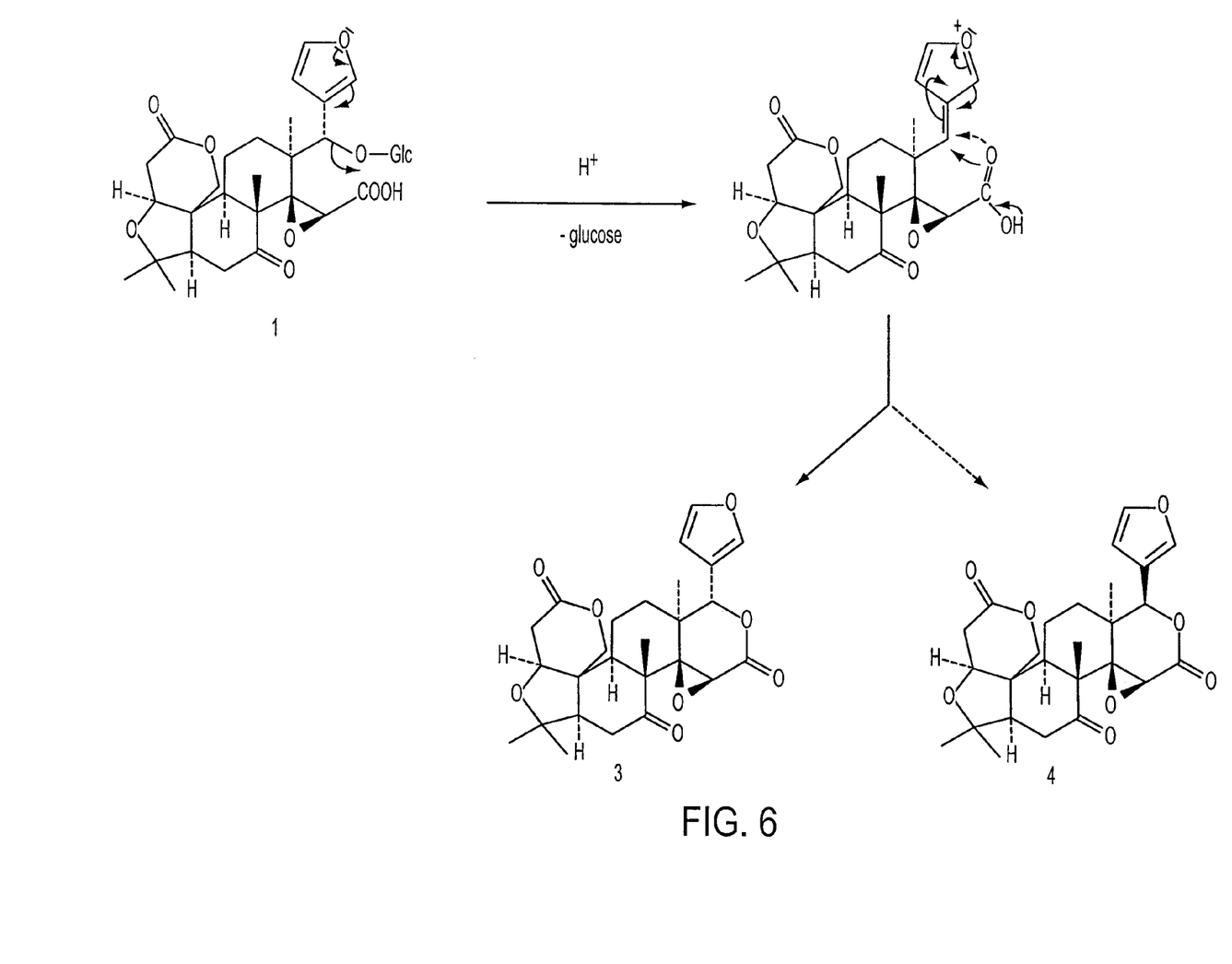
FIG. 6 illustrates a reaction sequence showing the hydrolytic degradation of limonin-17-β-D-glucopyranoside (1) to give the limonin (3) and $C_{17}$-epilimonin (4) via a furfurylidene carbo-cation as the key intermediate.

Although the inventors do not wish to be bound by theory, FIG. 6 illustrates a reaction pathway showing the formation of limonin (3) and isolimonin, or $C_{17}$-epilimonin (4), from limonin-17-β-D-glucopyranoside. As glucose is a good leaving group, the hexose is split off from the α-position of the furfurylidene group of 1 under acidic conditions, thus resulting in the release of a delocalized furfurylidene cation as the primary transient intermediate. Intramolecular cyclization induced by a nucleophilic attack of the carboxy function then gives rise to the limonin (3) bearing the furan ring in the α-orientation as well as isolimonin/$C_{17}$-epilimonin displaying the furan ring at C(17) in the β-orientation.

Also, it has been shown that incubation of limonin in aqueous solution having a pH of 3 does not produce significant quantity of isolimonin, so isolimonin is not formed by direct epimerization of limonin.

Example 4

Quantification of Limonin and Isolimonin in Orange Juice

Figure 7A:
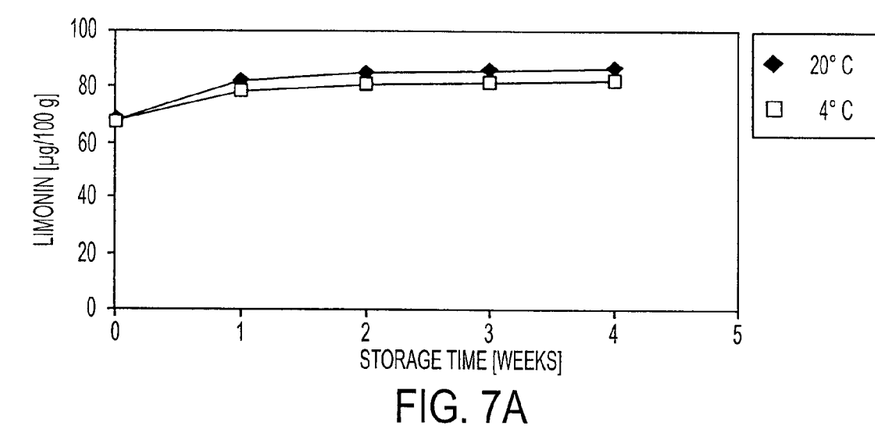
FIG. 7 illustrates the generation of limonin (A) and $C_{17}$-epilimonin (B) upon storage of an orange juice at 20° C. as a function of time.
Figure 7B:
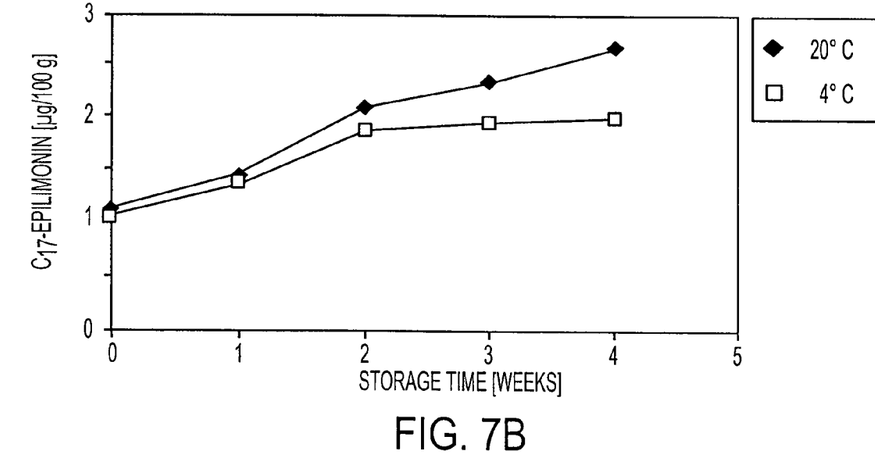

To investigate the generation of limonin and isolimonin/$C_{17}$-epilimonin during storage of orange juice, freshly squeezed orange juice (pH 3.5) was stored for up to four weeks at 4 and 20° C. and, then, limonin and isolimonin/$C_{17}$-epilimonin were quantitatively determined by means of HPLC-MS/MS using the MRM mode. As shown in FIG. 7A, the concentration of limonin in orange juice increased slightly during storage from 70.0 μg/100 g in the freshly squeezed juice to 80 and 85 μg/100 g when maintained for 2 weeks at 4 and 20° C., respectively. Storage of the orange juice induced also an increase in the concentration of $C_{17}$-epilimonin, e.g. in the samples maintained for four weeks at 4 and 20° C., respectively, a 1.5- or 2-fold increase of the amount of C17-epilimonin was observed (FIG. 7B). Comparing the storage-induced increase of the amount of limonin with that of isolimonin clearly demonstrated that the formation of limonin was more favored upon storage of the orange juice than that of its $C_{17}$-epimer, thus supporting the literature findings that during storage, limonoate A-ring lactone present in the juice is slowly converted to limonin upon acid catalysis.

Figure 8A:
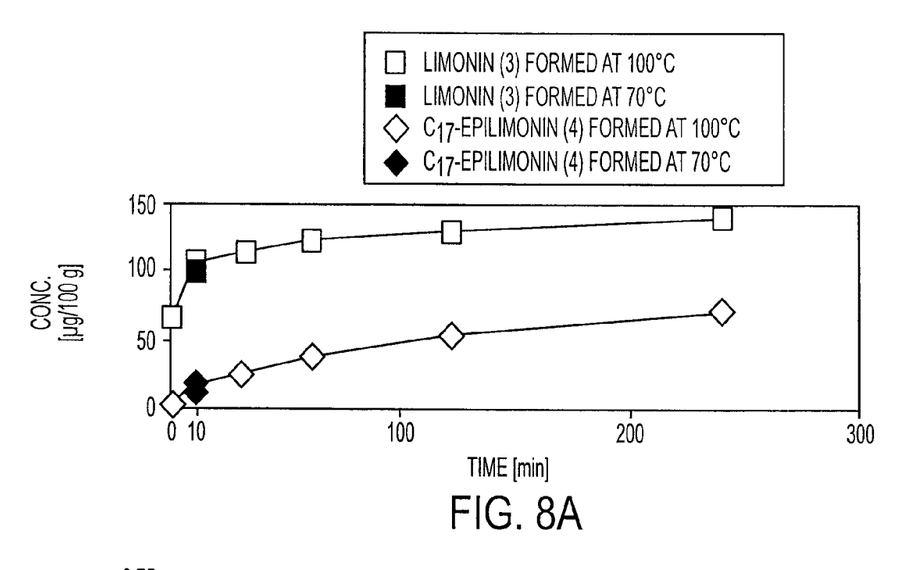
FIG. 8 illustrates the generation of limonin and $C_{17}$-epilimonin (A) and on the $C_{17}$-epilimonin/limonin ratio (B) upon thermal treatment of orange juice over time.

In a second set of experiments, the influence of heat treatment on the generation of limonin and isolimonin/$C_{17}$-epilimonin was investigated. To achieve this, freshly squeezed orange juice was thermally treated at 70° C. for 10 min and, in order to gain some insight into the maximal liberation rate of these compounds, at 95° C. for up to 240 min. HPLC-MS/MS (MRM) analysis revealed that the concentration of limonin and isolimonin in the freshly prepared, non-heated juice was 70.0 and 1.3 μg/100 g, respectively (FIG. 8A). Upon thermal treatment the concentrations of both terpenoids increased significantly, e.g. heating for 10 min at 70° C. induced an increase of the amount of isolimonin by a factor of five to reach a concentration of 6.1 μg/100 g, whereas the concentration of limonin reached a concentration of 100 μg/100 g.

Figure 8B:
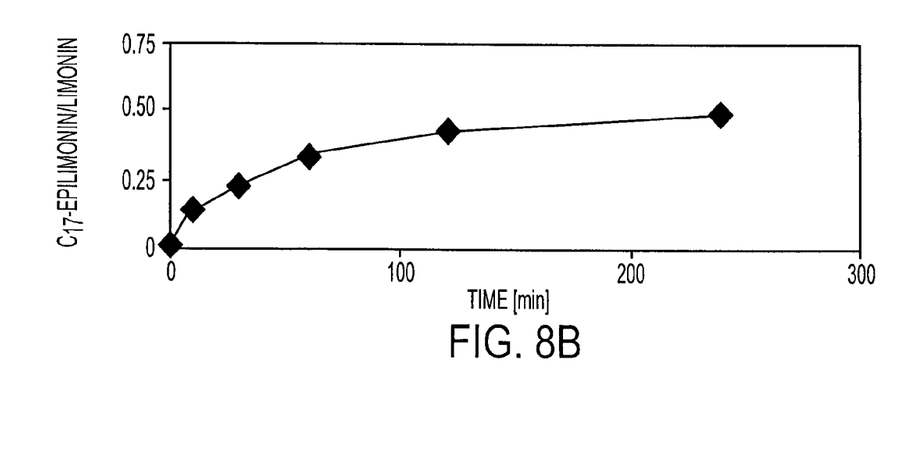

Heating the orange juice at 95° C. influenced the amounts of limonin and isolimonin even more. Already after heating the juice for 10 min at 95° C., the amount of $C_{17}$-epilimonin was increased by a factor of ten (FIG. 8A). After heating for 30 and 60 min, respectively, 20 and 30 μg/100 g of $C_{17}$-epilimonin were generated. Upon heating for 60 min, the concentration of limonin increased from 70 to 115 μg/100 g and approached a maximum value of 140 μg/100 g after 4 h. Calculation of the ratio between both limonoids in the heated orange juice samples revealed that the $C_{17}$-epilimonin/limonin ratio changes dramatically with increasing the heating time and reached a maximum of 0.50 after 240 min (FIG. 8B).

To make these determinations, oranges were halved and squeezed carefully by hand by means of a kitchen citrus juicer (Citromatic MPZ 22, Braun, Germany). Aimed at investigating the influence of cold-storage on the concentration of limonin and isolimonin in orange juice, aliquots (300 mL) of freshly squeezed orange juice were maintained at 4 and 20° C. for 4 weeks in the dark. In order to study the formation of limonin and isolimonin at elevated temperatures, aliquots (300 mL) of the freshly squeezed orange juice were thermally treated at 70° C. for 10 min or at 95° C. for up to 240 min.

For quantitative analysis, aliquots (8 g) of the fresh and treated orange juice, respectively, were centrifuged for 10 min at 3000 rpm, the non-soluble material was suspended and intimately mixed with water (8 mL), and again centrifuged for 10 min at 3000 rpm. The supernatants were combined and placed onto the top of a water-conditioned C 18-E SPE-cartridge (1 g, 5 μm, Phenomenex). After flushing with water (20 mL), the cartridge was dried by sucking a stream of nitrogen through it, and then eluted with methanol (20 mL). The methanolic effluent was freed from solvent in vacuum and made up to 3.0 mL with methanol. Aliquots (5 μL) were analyzed for limonin and isolimonin/$C_{17}$-epilimonin by means of LC-MS/MS on a Synergi Fusion, 150×2 mm i.d., 4 μm column (Phenomenex). To achieve this, chromatography was performed with a flow rate of 250 μL/min starting with a mixture (80/20, v/v) of 0.1% aqueous formic acid and acetonitrile, increasing the acetonitrile content to 40% within 10 min, then to 80% within 5 min, held for 5 min, and, finally, to 100% within 5 min. Using negative electrospray ionization, limonin and isolimonin/$C_{17}$-epilimonin was analyzed in the multiple reaction monitoring (MRM) mode using the mass transition m/z 469→229. Quantitative analysis was performed by comparing the peak areas obtained for the mass trace with those of defined standard solutions of limonin and $C_{17}$-epilimonin in methanol.

A final experiment was focused on the influence of the orange juice concentration process on the amounts of 3 and 4. To achieve this, the concentration of $C_{17}$-epilimonin was quantitatively analyzed in a fresh orange juice and a frozen orange juice concentrate produced from the same batch of orange juice by a 6.6-fold concentration. Whereas the orange juice contained isolimonin/$C_{17}$-epilimonin in amounts of 1.6 μg/100 g, about 21.0 μg/100 g of isolimonin were found in the corresponding frozen concentrated juice. Bearing in mind that the concentrate was produced by 6.6-fold concentration of the orange juice, 10.6 μg/100 g of the epimer were expected to be found in the concentrated juice. But a two times higher amount of 21.0 μg/100 g was present in the frozen concentrate, thus clearly demonstrating for the first time that $C_{17}$-epilimonin is formed in significant amounts during the manufacturing of frozen concentrated orange juice.

Example 5

Sensory Analysis

To study the influence of the chirality of C(17) on the sensory activity of these limonoids, bitter threshold concentrations were determined for limonin and $C_{17}$-epilimonin. These sensory studies revealed a bitter threshold concentration of 10.0 μg/L (water) for $C_{17}$-epilimonin which is rather close to that obtained for limonin (4.0 μmol/L), thus demonstrating a similar sensory activity of both triterpenoid lactone compounds.

To make these evaluations, eleven assessors (four women and seven men, age 23-39 years), who participated for at least two years in weekly training sessions, determined taste recognition threshold concentrations in bottled water (pH 5.1) by means of a three-alternative forced-choice method with ascending concentrations of the stimulus following the procedure reported previously in Stark, T.; Barenther, S.; Hofmann, T. (2005) J. Agric. Food Chem. 53:5407-5418.

The examples indicate that whereas ring-closure of limonoate A-ring lactone (2) only enables the formation of limonin (FIG. 1), the hydrolytic degradation of limonin-17-β-D-glucopyranoside (1) via the furfurylidene cation gives rise to limonin (3) and $C_{17}$-epilimonin (4) (FIG. 6). As only trace amounts of isolimonin were found to be generated upon cold-storage of orange juice but significantly higher amounts were released from its precursor limonin-17-β-D-glucopyranoside at elevated temperature, the $C_{17}$-epilimonin/limonin ratio might be a suitable marker enabling the analytical determination of the thermal input applied during orange juice processing.

As can be seen from FIG. 8, the isolimonin/limonin ratio increased from 0 to about 0.25 within about 20 minutes, and to about 0.40-0.45 in about 60 minutes at 100° C. Thus, the isolimonin/limonin ratio (also expressed as the $C_{17}$-epilimonin/limonin ratio) tends to indicate the severity of heating.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. A method for reducing the bitter taste of, and imparting fresh taste to, orange juice from concentrate comprising limonin, isolimonin, polymethoxylated flavones, and limonoid β-D-glucopyranosides, said method comprising treating orange juice from concentrate as follows:
   controlling the concentration of a blend of limonin and isolimonin in the orange juice to a level below the threshold taste level thereof and controlling the isolimonin/limonin ratio to less than about 0.25;
   controlling the concentration of polymethoxylated flavones in the orange juice to a level below the threshold taste level thereof;
   controlling the concentration of limonoid β-D-glucopyranosides in the orange juice to a level below the threshold taste level thereof; and
   increasing the Brix/Acid ratio of the orange juice by reducing the concentration of acid to lower than the acid concentration of the untreated juice, said acid selected from the group consisting of malic acid, citric acid, and blends thereof.

2. The method of claim 1 wherein the concentrations are controlled by a technique selected from the group consisting of reverse osmosis, ion exchange, distillation, or combinations thereof.

3. A treated orange juice from concentrate having a less-bitter taste than the orange juice from concentrate that is untreated, said treated orange juice comprising limonin, isolimonin, polymethoxylated flavones, and limonoid β-D-glucopyranosides, said treated orange juice having therein a concentration of a blend of limonin and isolimonin, less than the threshold taste concentration of the blend and the isolimonin/limonin ratio is less than about 0.25; polymethoxylated flavones at a level below the threshold taste level thereof, and limonoid β-D-glucopyranosides at a level below the threshold taste level thereof; and the treated orange juice has levels of acids selected from the group consisting of malic acid, citric acid, and blends thereof, lower than the concentration of acid in the untreated juice, wherein the treated orange juice from concentrate has a fresh taste.

* * * * *